United States Patent
Wilk

(10) Patent No.: US 7,572,824 B2
(45) Date of Patent: Aug. 11, 2009

(54) METHODS FOR MINIMIZING THIOAMIDE IMPURITIES

(75) Inventor: Bogdan K. Wilk, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/985,774

(22) Filed: Nov. 16, 2007

(65) Prior Publication Data

US 2008/0071083 A1 Mar. 20, 2008

Related U.S. Application Data

(62) Division of application No. 11/100,863, filed on Apr. 7, 2005, now Pat. No. 7,314,932.

(60) Provisional application No. 60/560,403, filed on Apr. 8, 2004.

(51) Int. Cl.
*A01N 43/16* (2006.01)
*A01N 43/32* (2006.01)
*A01N 43/38* (2006.01)
*A61K 31/35* (2006.01)
*A61K 31/385* (2006.01)
*A61K 31/40* (2006.01)
*C07D 209/02* (2006.01)
*C07D 207/00* (2006.01)
*C07D 207/30* (2006.01)
*C07D 279/04* (2006.01)
*C07D 279/06* (2006.01)
*C07D 265/12* (2006.01)

(52) U.S. Cl. ............ 514/419; 514/434; 514/456; 544/54; 544/92; 548/517; 548/518; 548/561; 548/466

(58) Field of Classification Search ............ 544/54, 544/92; 548/517, 518, 561, 466; 514/434, 514/456, 419
See application file for complete search history.

(56) References Cited

U.S. PATENT DOCUMENTS

| | | | |
|---|---|---|---|
| 4,997,950 A | 3/1991 | Murphy et al. | |
| 6,391,907 B1 | 5/2002 | Fensome et al. | |
| 6,407,101 B1 | 6/2002 | Collins et al. | |
| 6,417,214 B1 | 7/2002 | Ullrich et al. | |
| 6,436,929 B1 | 8/2002 | Zhang et al. | |
| 6,509,334 B1 | 1/2003 | Zhang et al. | |
| 7,132,445 B2 * | 11/2006 | Taveras et al. | 514/438 |
| 7,314,932 B2 | 1/2008 | Wilk | |
| 7,358,246 B2 * | 4/2008 | Wilk | 514/230.5 |
| 2008/0167299 A1 * | 7/2008 | Wilk | 514/230.5 |

OTHER PUBLICATIONS

Zhang et al., "Novel 6-aryl-1,4-dihydrobenzo[1,3]oxazine-2-thiones as Potent, Selective and Orally Active Nonsteroidal Progesterone Receptor Agonists", Bioorg. Med. Chem. Lett. 13:1313-1316 (Apr. 7, 2003).

* cited by examiner

*Primary Examiner*—James O Wilson
*Assistant Examiner*—Erich A Leeser
(74) *Attorney, Agent, or Firm*—Paul Carango, Esq.; Howson & Howson LLP

(57) ABSTRACT

Methods for minimizing the formation of thioamide compounds using decoy agents during reactions, such as thionations of carbonyl compounds containing nitrile groups, and the products thereby are provided.

23 Claims, No Drawings

METHODS FOR MINIMIZING THIOAMIDE IMPURITIES

CROSS-REFERENCE TO RELATED APPLICATION

This application is a divisional of U.S. patent application Ser. No. 11/100,863, filed Apr. 7, 2005, which claims the benefit of the priority of U.S. provisional patent application No. 60/560,403 filed Apr. 8, 2004, now abandoned.

BACKGROUND OF THE INVENTION

Progesterone receptor modulators can be prepared by thionation of carbonyl compounds. The thionation of benzoxazin-2-ones using either 2,4-bis(4-methoxyphenyl)-1,3-dithia-2,4-diphosphetane-2,4-disulfide (Lawesson's reagent) or phosphorous pentasulfide is known (U.S. Pat. No. 6,436,929). See, Scheme 1.

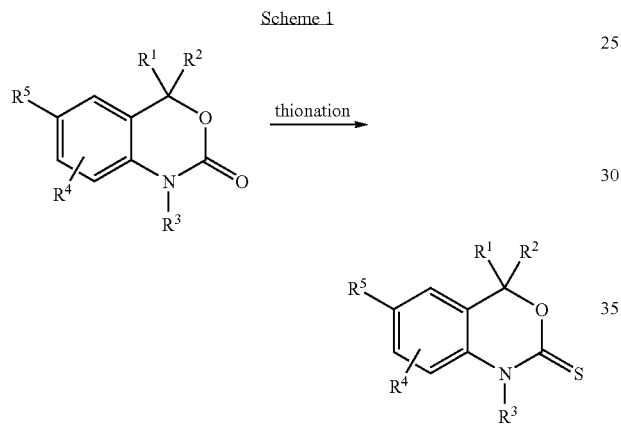

Such compounds are useful for contraception, hormone replacement therapy, synchronization of estrus, and in the treatment of conditions including hormone neoplastic diseases, adenocarcinomas, and carcinomas.

However, certain impurities formed during thionation are difficult to remove. What is needed in the art are methods for reducing or eliminating the formation of impurities.

SUMMARY OF THE INVENTION

In one aspect, the present invention provides methods for preventing, reducing or minimizing the formation of thioamide impurities.

In another aspect, the present invention provides methods for preventing, reducing or minimizing the formation of thioamide impurities using a decoy agent.

In a further aspect, the present invention provides methods for preventing, reducing or minimizing the formation of thioamide impurities during thionation of a carbonyl compound comprising a nitrile group.

In yet another aspect, the present invention provides methods for preventing the formation of thioamide impurities of the structure, wherein Y, $R^7$-$R^9$ are defined below:

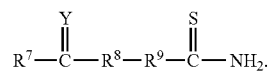

In still a further aspect, the present invention provides methods for preventing the formation of thioamide impurities of the structure, wherein $R^1$, $R^7$, and $R^8$ are defined below:

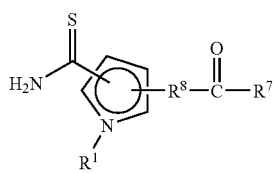

In another aspect, the present invention provides methods for preventing the formation of thioamide impurities of the structure, wherein $R^1$-$R^5$ are defined below:

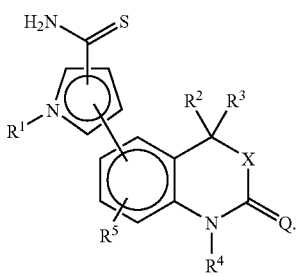

Other aspects and advantages of the present invention are described further in the following detailed description of the preferred embodiments thereof.

DETAILED DESCRIPTION OF THE INVENTION

The present invention provides methods for minimizing the formation of thioamide compounds using decoy agents. Specifically, the present invention provides methods for adding decoy agents to avoid undesirable side reactions.

I. Definitions

The term "alkyl" is used herein to refer to both straight- and branched-chain saturated aliphatic hydrocarbon groups having 1 to about 10 carbon atoms, and desirably 1 to about 8 carbon atoms. The term "alkenyl" is used herein to refer to both straight- and branched-chain alkyl groups having one or more carbon-carbon double bonds and containing about 2 to about 10 carbon atoms. Desirably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Desirably, the term alkynyl refers to an alkyl group having 1 or 2 carbon-carbon triple bonds and having 2 to about 6 carbon atoms.

The term "cycloalkyl" is used herein to refer to an alkyl group as previously described that is cyclic in structure and has about 4 to about 10 carbon atoms, and desirably about 5 to about 8 carbon atoms.

The terms "substituted alkyl", "substituted alkenyl", "substituted alkynyl", and "substituted cycloalkyl" refer to alkyl, alkenyl, alkynyl, and cycloalkyl groups, respectively, having one or more substituents the same or different including, without limitation, halogen, CN, OH, $NO_2$, amino, aryl, heterocyclic, alkoxy, aryloxy, alkylcarbonyl, alkylcarboxy, and arylthio which groups are optionally substituted. These substituents can be attached to any carbon of an alkyl, alkenyl, or alkynyl group provided that the attachment constitutes a stable chemical moiety.

The term "aryl" as used herein as a group or part of a group refers to an aromatic system which can include a single ring or multiple aromatic rings fused or linked together where at least one part of the fused or linked rings forms the conjugated aromatic system e.g. having 6 to 14 carbon atoms. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents the same or different including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Desirably, a substituted aryl group is substituted with 1, 2, 3 or 4 substituents.

The term "heterocyclic" or "heteroaryl" as used herein refers to a stable 4- to 10-membered monocyclic or multicyclic heterocyclic ring which is saturated, partially unsaturated, or wholly unsaturated. The heterocyclic ring has carbon atoms and one or more heteroatoms including nitrogen, oxygen, and sulfur atoms. Desirably, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring e.g. of 6 to 14 carbon atoms. The heterocyclic ring can be attached to the aryl ring through a heteroatom or carbon atom provided the resultant heterocyclic ring structure is chemically stable.

A variety of heterocyclic or heteroaryl groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" or "substituted heteroaryl" as used herein refers to a heterocyclic group having one or more substituents the same or different including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. Desirably, a substituted heterocyclic group is substituted with 1, 2, 3 or 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" includes hydroxyalkyl and as used herein refers to the alkylOH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O) (alkyl) group, where the point of attachment is through the carbon-atom of the carbonyl moiety and the alkyl group is optionally substituted.

The term "alkylcarboxy" as used herein refers to the C(O) O(alkyl) group, where the point of attachment is through the carbon-atom of the carboxy moiety and the alkyl group is optionally substituted.

The term "aminoalkyl" includes alkylamino and as used herein refers to both secondary and tertiary amines where the point of attachment is through the nitrogen-atom and the alkyl groups are optionally substituted. The alkyl groups can be the same or different.

The term "thioalkoxy" or "thioalkyl" as used herein refers to the S(alkyl), where the point of attachment is through the sulfur-atom and the alkyl group is optionally substituted.

The term "halogen" as used herein refers to Cl, Br, F, or I groups.

The term "amide" as used herein refers to the $C(O)NH_2$ group, where the point of attachment is through the carbon-atom. Similarly, the term "thioamide" as used herein refers to a $C(S)NH_2$ substituent.

The term "nitrile" or "cyano" as used herein refers to a CN group.

The term "ketone" as used herein refers to the C(O) group, where the points of attachment are through the carbon-atom. Similarly, the term "aldehyde" as used herein refers to the C(O)H, where the point of attachment is through the carbon-atom.

The term "lactone" as used herein refers to a ring having an ester moiety in the backbone of the ring. The lactone ring can be optionally substituted with any substituent that forms a stable bond to the ring.

The terms "carbamate" and "urethane" are used herein interchangeably to refer to a N—C(O)O group, where the point of attachments are through the nitrogen and oxygen atoms.

The term "carbonate" is used herein to refer to a O—C (O)—O group.

The term "enone" is used therein to refer to a molecule that contains an alkene group, i.e., —C=C—, and a ketone group. Desirably, the enone is C=C—C(O), where the point of attachments are through the carbon-atom of the alkene and the carbon-atom of the carbonyl.

The term "enaminone" is used herein to refer to a molecule that contains the —N—C=C—C(O) group, where the point of attachments are through the carbon-atom of the alkene and the carbon-atom of the carbonyl.

The term "purified" or "pure" as used herein refers to a compound that contains less than about 10% impurity. Desirably, the term "purified" or "pure" refers to a compound that contains less than about 5% impurity, more desirably, less than about 2% impurity, and most desirably less than 1% impurity. The term "purified" or "pure" can also refer to a compound that contains about 0% impurity. In one embodiment, the impurity is a thioamide.

II. The Decoy Agent

Methods are provided for preventing or minimizing the formation of impurities such as thioamides. Desirably, the present invention provides methods for preventing or minimizing the formation of thioamide impurities during thionations of carbonyl compounds containing nitrile groups. The method utilizes a decoy agent containing a nitrile group. See, Scheme 2.

Scheme 2

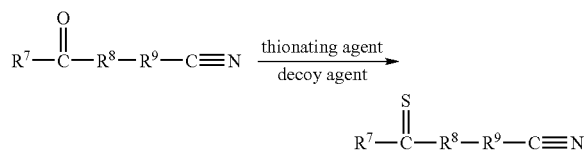

Without wishing to be bound by theory, the inventors have hypothesized that thioamide impurities are formed by addition of hydrogen sulfide ($H_2S$), a $H_2S$ by-product, or a dithiaphosphetane by-product such as a Lawesson's reagent by-product, among others, to a nitrile moiety. See, Scheme 3. Therefore, the inventors have found that the addition of a decoy agent in the reaction mixture that prevents or minimizes the formation of the thioamide impurity is advantageous.

Scheme 3

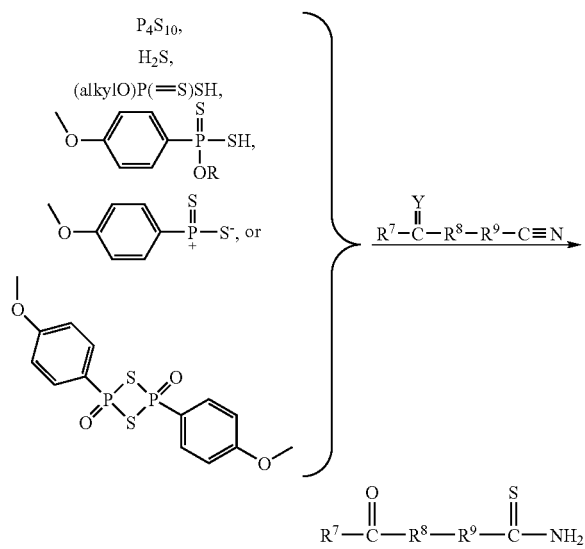

The decoy agent used in the present invention competes with the nitrile substituent of the carbonyl compound during thionation. In one embodiment, the decoy agent competes with the nitrile substituent for reaction with $H_2S$, an $H_2S$ by-product formed during the reaction, or a Lawesson's agent by-product formed during thionation of a carbonyl compound having a nitrile compound attached thereto. However, the decoy agent desirably reacts only minimally or does not react with actual thionating reagent.

The term "decoy agent" as used herein is distinguishable from "scavengers", "trapping agents" or "mopping reagents".

As known to those of skill in the art, scavengers, trapping agents or mopping reagents are used to remove excess reagents, products, or other formed impurities. For example, $H_2S$ can be scavenged with lead acetate, trapped with molecular sieves, or mopped with water. A decoy agent, however, is intentionally added to redirect any side reactions and is a sacrificial reagent which protects the product from being a source of a contaminant.

One of skill in the art would readily be able to select a suitable decoy agent depending on the reaction conditions, cost of decoy agent, reactivity of the decoy agent, reactivity of the carbonyl compound, and reactivity of the carbonyl group of the carbonyl compound. Desirably, the decoy agent is similar in structure to the nitrile group of the carbonyl compound.

Electron withdrawing substituents attached to the decoy agent can increase the reactivity of the decoy agent, and specifically, the reactivity of a nitrile group on the decoy agent. Desirably, the electron withdrawing substituent includes a halogen, and more desirably chlorine. Desirably, the decoy agent is chloroacetonitrile ($ClCH_2CN$), trichloroacetonitrile, or 1,3-dicyanobenzene.

In one embodiment, the carbonyl compound contains a very reactive carbonyl group and a less reactive nitrile group, whereby the carbonyl group easily reacts with the thionating compound. In this case, a less reactive decoy agent can be utilized during the thionation reaction to prevent formation of the thioamide impurity. However, more reactive decoy agents can be utilized with reactive carbonyl compounds. Typically, acetonitrile is utilized if the carbonyl group of the carbonyl compound easily reacts with the thionating agent.

In another embodiment, the carbonyl compound contains a reactive carbonyl group and a reactive nitrile group. In this case, a moderately reactive decoy agent can be utilized during the thionation reaction to prevent formation of the thioamide impurity. Typically, moderately reactive decoy agents such as benzonitrile, p-chlorobenzonitrile, p-methylbenzonitrile, 1,3-dicyanobenzene, 3- and 4-cyanopyridines and malononitrile can be utilized.

In a further embodiment, the carbon-containing compound contains a less reactive carbonyl group and a highly reactive nitrile. In this case, a highly reactive decoy agent can be utilized during the thionation reactive to prevent formation of the thioamide impurity. Typically, highly reactive decoy agents such as N-methyl-2-pyrrolecarbonitrile, 2-thiophenecarbonitrile, 2-cyanopyridine, chloroacetonitrile and trichloroacetonitrile can be utilized.

Examples of decoy agents that can be used according to the present invention include, without limitation, aryl nitrites including benzonitrile, p-chlorobenzonitrile, p-methoxybenzonitrile, p-ethoxybenzonitrile, o-nitrobenzonitrile, p-acetylbenzonitrile, p-methylbenzonitrile, p-fluorobenzonitrile, and 1,3-dicyanobenzene; aliphatic nitrites such as acetonitrile ($CH_3CN$), propionitrile, butyronitrile, iosbutyronitrile, chloroacetonitrile, trichloroacetonitrile and malononitrile; a nitrile compound having one or more electron withdrawing substituents; or heteroaryl nitrites including N-methyl-2-pyrrolecarbonitrile, 2-thiophenecarbonitrile, and 2-cyanopyridine. However, while some decoy agents may be utilized, it may be cost-prohibitive for the use thereof. For example, $CH_3CN$ is an inexpensive, low-boiling, common reagent with twice the moles of nitrile groups as compared to N-methyl-2-pyrrolecarbonitrile. Further, while 2-thiophenecarbonitrile is twice as reactive as benzonitrile, it is considerably more expensive. More desirably, the decoy agent is similar in structure to N-methyl-2-pyrrolecarbonitrile and is acetonitrile or 2-thiophenecarbonitrile.

A molar excess of the decoy agent is typically added to the reaction mixture, where the reaction mixture contains a compound having a nitrile moiety, i.e., moles of decoy agent are greater than moles of nitrile compound. However, less than a 1:1 ratio of decoy agent to the compound having a nitrile moiety, i.e., moles of decoy agent are less than moles of nitrile compound, can also be utilized. In one embodiment, greater than an about 10 molar excess of decoy agent is utilized. In another embodiment, greater than an about 20 molar excess; in a further embodiment, greater than an about 40 molar excess; and in still another embodiment, greater than a 100 molar excess of decoy agent is utilized. In one embodiment, the decoy agent can be utilized as the solvent. One of skill in the art would readily be able to determine the amount of decoy agent required depending on the reaction being performed, reagents utilized, and reactivity of the decoy agent.

III. The Method of the Invention

The present invention thereby provides methods for preventing or minimizing the formation of thioamide impurities. Typically, the thioamide impurities formed according to the present invention include thioamide groups attached at any location on the backbone of the thioamide molecule.

In one embodiment, the thioamide impurity contains a thioamide group of the structure:

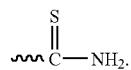

In another embodiment, the thioamide impurity is of the structure:

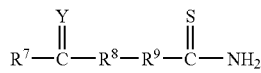

wherein Y is O or S; $R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl; $R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or $R^7$ and $R^8$ are fused to form (i) a saturated carbon-based 4 to 8 membered ring; (ii) an unsaturated carbon-based 4 to 8 membered ring; or (iii) a 4 to 8 heterocyclic ring containing 1 to 3 heteroatoms selected from among O, N, and S; wherein rings (i)-(iii) are optionally substituted by 1 to 3 substituents selected from among H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl; $R^9$ is absent, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; $R^{10}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^{11}$, and $N(R^{11})_2$; and $R^{11}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

In a further embodiment, the thioamide impurity is of the structure:

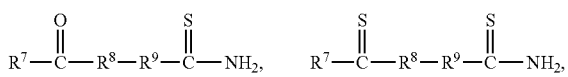

or a combination thereof, wherein, $R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl; $R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or $R^7$ and $R^8$ are fused to form (i) a saturated carbon-based 4 to 8 membered ring; (ii) an unsaturated carbon-based 4 to 8 membered ring; or (iii) a 4 to 8 heterocyclic ring containing 1 to 3 heteroatoms selected among O, N, and S; wherein rings (i)-(iii) are optionally substituted by 1 to 3 substituents selected from among H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl; $R^9$ is absent, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; $R^{10}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^{11}$, and $N(R^{11})_2$; and $R^{11}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

In still a further embodiment, the thioamide impurity contains a thioamide group that is attached to a pyrrole ring or to a substituent of a pyrrole ring. The thioamide impurity can therefore have the following thioamide substituent, where $R^1$ is $C_1$ to $C_6$ alkyl or substituted $C_1$ to $C_6$ alkyl.

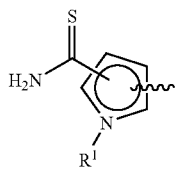

In another embodiment, the thioamide impurity is of the structure:

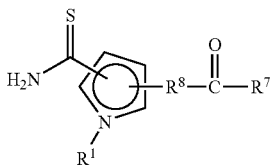

wherein, $R^1$ is selected from among $C_1$ to $C_6$ alkyl or substituted $C_1$ to $C_6$ alkyl. and $R^7$ and $R^8$ are defined above.

In still a further embodiment, the thioamide impurity is of the structure:

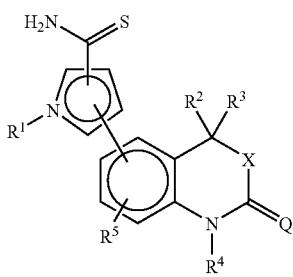

I wherein, $R^1$ is selected from among $C_1$ to $C_6$ alkyl or substituted $C_1$ to $C_6$ alkyl. $R^2$ and $R^3$ are independently selected from among H, $C_1$ to $C_6$ alkyl, or substituted $C_1$ to $C_6$ alkyl; or $R^2$ and $R^3$ are fused to form a ring including —$CH_2(CH_2)_n$$CH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—, n is 1, 2, 3, 4, or 5, p is 1, 2, 3, or 4, and q is 1, 2, 3, or 4; $R^4$ is selected from among H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, or substituted $C_2$ to $C_6$ alkynyl; $R^5$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl; $R^6$ is selected from among H or $C_1$ to $C_6$ alkyl; Q is selected from among O or S; and X is absent or is selected from among O or S.

In still a further embodiment, the thioamide impurity is of the structure:

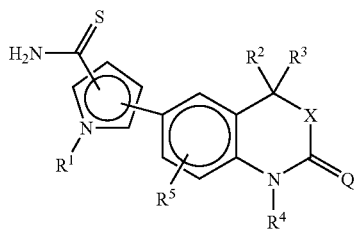

wherein, $R^1$-$R^5$, X, and Q are defined above.

The carbonyl compound containing a nitrile group utilized in the present invention contains at least one carbonyl and at least one nitrile group. The present invention also provides for carbonyl compounds having more than 1 carbonyl group, e.g., 2, 3, 4, 5, or 5 carbonyl groups and more, more than 1 nitrile group, e.g., 2, 3, 4, or 5 nitrile groups and more, or a combination thereof.

In one embodiment, the carbonyl compound is of the structure:

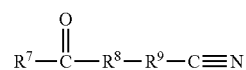

wherein, $R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl; $R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or $R^7$ and $R^8$ are fused to form (i) a saturated carbon-based 4 to 8 membered ring; (ii) an unsaturated carbon-based 4 to 8 membered ring; or (iii) a 4 to 8 heterocyclic ring containing 1 to 3 heteroatoms selected from among O, N, and S; wherein rings (i)-(iii) are optionally substituted by 1 to 3 substituents selected from among H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl; $R^9$ is absent, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; $R^{10}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^{11}$, and $N(R^{11})_2$; and $R^{11}$ is selected from among H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

In a further embodiment, the carbonyl compound is of the structure:

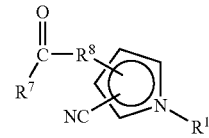

wherein, $R^1$ is $C_1$ to $C_6$ alkyl or substituted $C_1$ to $C_6$ alkyl; $R^7$ and $R^8$ are defined above.

In yet another embodiment, the carbonyl compound is of the structure:

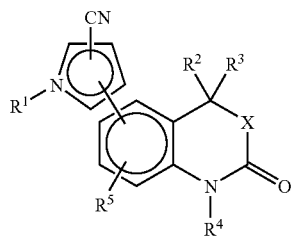

wherein, $R^1$ is $C_1$ to $C_6$ alkyl or substituted $C_1$ to $C_6$ alkyl; $R^2$ and $R^3$ are, independently, H, $C_1$ to $C_6$ alkyl, or substituted $C_1$ to $C_6$ alkyl; or $R^2$ and $R^3$ are fused to form a ring comprising —$CH_2(CH_2)_nCH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—; n is 1 to 5; p is 1 to 4; q is 1 to 4; $R^4$ is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, or substituted $C_2$ to $C_6$ alkynyl; $R^5$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl; $R^6$ is H or $C_1$ to $C_6$ alkyl; X is O, S, or absent; or a pharmaceutically acceptable salt thereof.

In still a further embodiment, the carbonyl compound is of the structure:

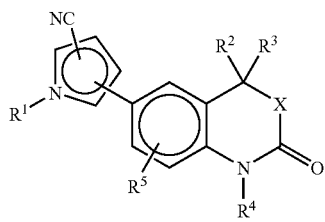

wherein, $R^1$-$R^5$ and X are defined above.

Typically, the decoy agent utilized is in the presence of a solvent. One of skill in the art would readily be able to select a suitable solvent for use with the decoy agent depending on the other reagents utilized and reaction conditions, among others. Desirably, the solvent does not react with any of the reagents utilized in the reaction and does not contain any peroxides. In one embodiment, the solvent includes tetrahydrofuran (THF), 1,2-dimethoxyethane (DME), toluene, and methylene chloride, among others.

The decoy agent can be utilized at any temperature that facilitates the reaction and can readily be determined by one of skill in the art. Desirably, the decoy agent is utilized at least room temperature, and more desirably at the boiling point of the solvent.

When the decoy agent is utilized in a thionation reaction, the reaction is performed using a thionating agent. Several thionating agents that replace O-atoms with S-atoms are known in the art and include, without limitation, phosphorus pentasulfide ($P_4S_{10}$), hydrogen sulfide, Lawesson's reagent, and dialkyldithiophosphates such as diethyldithiophosphate (See, Phosphorous and Sulfur 1985, 25, 297). See, Scheme 4.

Scheme 4

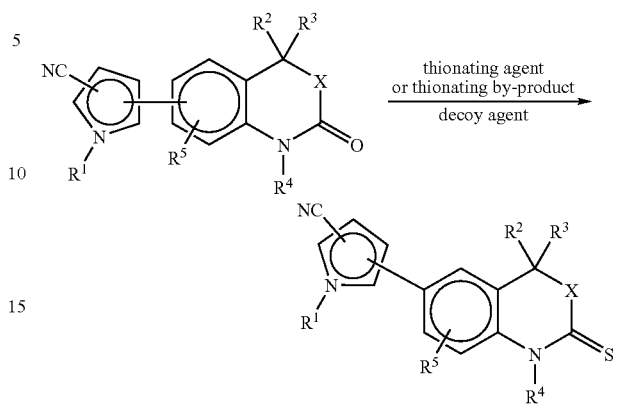

Desirably, the thionating agent does not react with the decoy reagent. The thionation can also be performed with thionating by-products that agents are formed during the reaction and include:

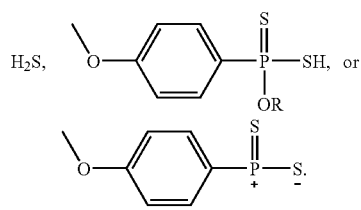

In one embodiment, the present invention provides a method for preventing or minimizing the formation of thioamide impurities during thionation of a nitrile compound containing a carbonyl group including performing the thionation in the presence of a decoy agent having a nitrile group.

In another embodiment, the present invention provides a product prepared by the method of the present invention.

The resulting compounds of the present invention can be formulated in a physiologically compatible carrier and used as PR modulators as described in U.S. Pat. Nos. 6,509,334; 6,391,907; 6,417,214; and 6,407,101, which are hereby incorporated by reference. The invention further provides kits comprising the product.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Reactivity of Decoy Agents

One mmol of the aromatic nitrile decoy agents set forth in Table 1 were reacted at reflux with the thionating agent diethyl dithiophosphate (0.2 mL) in wet THF (6 mL) to give the respective thioamides.

TABLE 1

| Nitrile | % Conversion to Thioamide* |
|---|---|
| 2-thiophenecarbonitrile | 100 |
| benzonitrile | 55 |
| p-chlorobenzonitrile | 67 |
| p-methoxybenzonitrile | 45 |
| o-nitrobenzonitrile | 25 |
| p-acetylbenzonitrile | 57 |
| p-methylbenzonitrile | 52 |
| p-fluorobenzonitrile | 68 |

*% conversion as determined by gas chromatography/mass spectroscopy (GC/MS)

This example illustrates that 2-thiophenecarbonitrile was the most reactive with the thionating agent.

Example 2

Use of Decoy Agent During Thionation

Acetonitrile (21 kg, 512 mol) was utilized as decoy agent in a thionation of 5-(4,4-dimethyl-2-oxo-1,4-dihydro-benzoxazin-6-yl)-1-methyl-1H-pyrrole-2-carbonitrile (34 kg, 126 mol), i.e., a 4:1 molar ratio, using Lawesson's reagent (28.3 kg, 70 mol) in DME (505 kg) at reflux to give 5-(4,4-dimethyl-2-thioxo-1,4-dihydro-benzoxazin-6-yl)-1-methyl-1H-pyrrole-2-carbonitrile (26.7 kg; 74% yield).

The crude reaction mixture of 5-(4,4-dimethyl-2-thioxo-1,4-dihydro-benzoxazin-6-yl)-1-methyl-1H-pyrrole-2-carbonitrile contained only about 2.6% of 5-(4,4-dimethyl-2-thioxo-1,4-dihydro-benzoxazine)-1-methyl-pyrrole-2-thioamide impurity. After recrystallization, the purified 5-(4,4-dimethyl-2-thioxo-1,4-dihydro-benzoxazin-6-yl)-1-methyl-1H-pyrrole-2-carbonitrile was about 99.90% pure.

When the reaction was performed in the absence of the decoy agent, the thioamide impurity was present at about 11 to about 12%.

Example 3

Competition Between 2-Thiophenecarbonitrile and Alkyl Nitriles

2-Thiophenecarbonitrile (1 mmol) was reacted at reflux with diethyl dithiophosphate (200 μL) in wet THF (6 mL) and in the presence of the aliphatic nitrites (1 mmol) set forth in Table 2. The conversion of the undesired thiophene-2-carbothioic acid amide was then measured.

TABLE 2

| Nitrile | % Conversion to Thioamide* |
|---|---|
| None | 75 |
| Trichloroacetonitrile | 46 |
| Chloroacetonitrile | 40 |
| Malononitrile | 54 |
| Acetonitrile | 71 |

*Technical grade of diethyldithiophosphate was utilized.

This example illustrates that conversion of a reactive nitrile, such as 2-thiophene carbonitrile, to the thioamide impurity is high when no decoy agent is utilized. However, conversion to the thioamide impurity is decreased when decoy agents are utilized.

Example 4

Competition Between 2-Thiophenecarbonitrile and Acetonitrile

2-Thiophenecarbonitrile (1 mmol) was reacted at reflux with diethyl dithiophosphate (200 μL) in wet THF and acetonitrile using the molar equivalents set forth in Table 3. The conversion of the undesired thiophene-2-carbothioic acid amide was then measured.

TABLE 3

| Molar Equivalent of Acetonitrile | % Conversion to Thioamide |
|---|---|
| 1 | 71 |
| 10 | 53 |
| 20 | 37 |
| 40 | 25 |
| 120** | 19 |

*Volume of THF and MeCN retained at 6 mL by adjusting the amount of MeCN and THF.
**Neat acetonitrile (no THF solvent present)

This example illustrates that conversion to the thioamide impurity decreased as the amount of acetonitrile increased.

Example 5

Effect of Acetonitrile on the Formation of Thioamide Impurities

The nitrile set forth in Table 4 was reacted at reflux with diethyl dithiophosphate (200 μL) in wet THF (5 mL) and acetonitrile (1 mL=20 molar equivalents). The control set contained 6 mL THF and no acetonitrile. After 5 hours at 66° C., the mixtures were subjected to GC/MS analysis to detect the presence of thioamide impurity.

TABLE 4

| | % Conversion to Thioamide | |
|---|---|---|
| Nitrile | with acetonitrile | without acetonitrile |
| 2-thiophenecarbonitrile | 33 | 78 |
| benzonitrile | 11 | 43 |
| p-acetylbenzonitrile | 11 | 45 |
| p-methoxybenzonitrile | 2 | 38 |
| p-chlorobenzonitrile | 13 | 51 |
| 1,4-dicyanobenzene | 34 | 67 |

This example illustrates that conversion to the thioamide impurity was suppressed in samples containing acetonitrile. Further, samples containing acetonitrile and p-methoxybenzonitrile had very little conversion to the thioamide impurity.

Example 6

Use of Decoy Agent During Thionation

A 2-L flask was charged with 1,2-dimethoxyethane (2.1 L) and 5-(spiro[cyclohexane-1,3'-[3H]indole]-2'-oxo-5'-yl)-1H-pyrrole-1-methyl-2-carbonitrile (150 g, 0.49 mol), followed by Lawesson's reagent (119 g, 0.295 mol) and acetonitrile (0.3 L, 5.75 mol), i.e., a 12:1 molar ratio of decoy agent to nitrile compound. The suspension was heated to reflux and kept for 1 hour. Upon cooling to ambient temperature, water (2.51 L) was added to the suspension at a rate to maintain the temperature below 30° C. The yellow-greenish precipitate was filtered on a fritted funnel. The solid was transferred back to the reaction flask and slurried in water (0.75 L) overnight. The yellow suspension was filtered, washed with water (0.45 L) and dried to give 154 g (98% yield, 99.0% purity by HPLC area, mp 269-271.5° C., 0.60% thioamide impurity) of 5-(2'-thioxospiro[cyclohexane-1,3'-[3H]indol]-5'-yl)-1-methyl-1H-pyrrole-2-carbonitrile.

Example 7

Use of Decoy Agent During Thionation (Scale-Up)

In this example, a larger scale production of [5-(2'-thioxospiro[cyclohexane-1,3'-[3H]indol]-5'-yl)-1-methyl-1H-pyrrole-2-carbonitrile] was performed.

A 100-gal vessel was charged with 1,2-dimethoxyethane (155.1 kg, 178.8 L) and 5-(spiro[cyclohexane-1,3'-[3H]indole]-2'-oxo-5'-yl)-1H-pyrrole-1-methyl-2-carbonitrile (12.78 kg), followed by Lawesson's reagent (10.14 kg) and acetonitrile (20.1 kg, 25.6 L). The contents of the vessel was heated to reflux and kept for 1 hour. The orange-brown solution was cooled to 70° C. and a sample was withdrawn for the reaction completion test that showed less than 0.2% of the starting material. The batch was cooled to ambient temperature and water (213.9 kg) was charged at a rate to maintain temperature between 23 and 29° C. The yellow-greenish suspension was filtered on a 0.3 SQM PSL filter/dryer. The solids were slurried in water (63.9 kg) on the filter/dryer for 15 minutes. The yellow suspension was transferred into a 100-gal vessel and the filter was rinsed with water (2×10 kg) into the vessel. The slurry was stirred at 18-26° C. for 12 hours, filtered on a 0.3 SQM PSL filter/dryer and washed with water (2×19.2 kg). The solids were dried in a vacuum oven at initially 20-30° C. and then at 45° C. to give 12.8 kg of crude 5-(2'-thioxospiro[cyclohexane-1,3'-[3H]indol]-5'-yl)-1-methyl-1H-pyrrole-2-carbonitrile (95% yield, 0.45% thioamide impurity).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A product prepared by thionating a carbonyl compound comprising a nitrile group in the presence of a decoy agent comprising a nitrile group, wherein the moles of said decoy agent is greater than the moles of said carbonyl compound; and
wherein said product contains reduced or no thioamide impurities.

2. A product prepared by thionating a carbonyl compound comprising a nitrile group in the presence of a decoy agent comprising a nitrile group, wherein the moles of said decoy agent is less than the moles of said carbonyl compound; and
wherein said product contains reduced or no thioamide imnurities.

3. A method of thionating a carbonyl compound comprising a nitrile group in the presence of a decoy agent comprising a nitrile group,
wherein reduced or no thioamide impurities of the structure are formed:

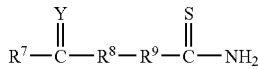

wherein:
Y is O or S;
R$^7$ is H, NH$_2$, NHR$^{10}$, N(R$^{10}$)$_2$, C(O)R$^{10}$, C(S)R$^{10}$, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ thioalkyl, substituted C$_1$ to C$_6$ thioalkyl, C$_1$ to C$_6$ alkoxy, substituted C$_1$ to C$_6$ alkoxy, aryl, substituted aryl, heteroaryl, or substituted heteroaryl;
R$^8$ is C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, or substituted heteroaryl; or
R$^7$ and R$^8$ are fused to form:
(i) a saturated carbon-based 4 to 8 membered ring;
(ii) an unsaturated carbon-based 4 to 8 membered ring; or
(iii) a 4 to 8 heterocyclic ring containing 1 to 3 heteroatoms selected from the group consisting of O, N, and S;
wherein rings (i)-(iii) are optionally substituted by 1 to 3 substituents selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, substituted heteroaryl, C$_1$ to C$_6$ aminoalkyl, and substituted C$_1$ to C$_6$ aminoalkyl;
R$^9$ is absent, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, or substituted heteroaryl;
R$^{10}$ is selected from the group consisting of H, C$_1$ to C$_6$ alkyl, substituted C$_1$ to C$_6$ alkyl, aryl, substituted aryl, C$_1$ to C$_6$ alkoxy, substituted C$_1$ to C$_6$ alkoxy, C$_1$ to C$_6$ aminoalkyl, substituted C$_1$ to C$_6$ aminoalkyl, C$_1$ to C$_6$ thioalkyl, substituted C$_1$ to C$_6$ thioalkyl, NH$_2$, NHR$^{11}$, and N(R$^{11}$)$_2$; and
R$^{11}$ is selected from the group consisting of H, C$_1$ to C$_6$ alkyl, substituted C$_1$ to C$_6$ alkyl, aryl, substituted aryl, C$_1$ to C$_6$ alkoxy, substituted C$_1$ to C$_6$ alkoxy, C$_1$ to C$_6$ aminoalkyl, substituted C$_1$ to C$_6$ aminoalkyl, C$_1$ to C$_6$ thioalkyl, substituted C$_1$ to C$_6$ thioalkyl, and NH$_2$.

4. The method according to claim 3, wherein said thioamide impurity is of the structure:

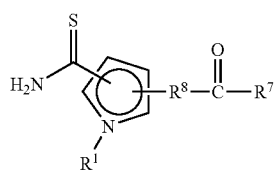

wherein:
R$^1$ is C$_1$ to C$_6$ alkyl or substituted C$_1$ to C$_6$ alkyl;

$R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl;

$R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or $R^7$ and $R^8$ are fused to form:
(i) a saturated carbon-based 4 to 8 membered ring;
(ii) an unsaturated carbon-based 4 to 8 membered ring; or
(iii) a 4 to 8 heterocyclic ring containing 1 to 3 heteroatoms selected from the group consisting of O, N, and S;
wherein rings (i)-(iii) are optionally substituted by 1 to 3 substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl;

$R^{10}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalky, $C_1$ to $C_6$ thioalkyl, substituted $C_1$ to $C_6$ thioalkyl, $NH_2$, $NHR^{11}$, and $N(R^{11})_2$; and $R^{11}$ is selected from the group consisting of H, $C_1$ to $C_6$ alkyl, substituted $C_1$ to $C_6$, alkyl, aryl, substituted aryl, $C_1$ to $C_6$ alkoxy, substituted $C_1$ to $C_6$ alkoxy, $C_1$ to $C_6$, aminoalkyl, substituted $C_1$ to $C_6$ aminoalkyl, $C_1$ to $C_6$ thioalkyl, substituted $C_1$ to $C_6$ thioalkyl, and $NH_2$.

5. The method according to claim 3, wherein said thioamide impurity is of the structure:

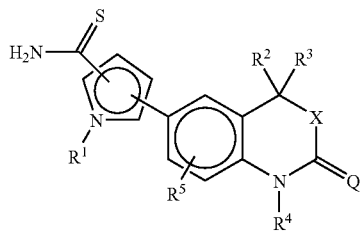

wherein:
$R^1$ is $C_1$ to $C_6$ alkyl or substituted $C_1$ to $C_6$ alkyl;
$R^2$ and $R^3$ are, independently, H, $C_1$ to $C_6$ alkyl, or substituted $C_1$ to $C_6$ alkyl;
or $R^2$ and $R^3$ are fused to form a ring comprising —$CH_2$ ($CH_2$)$_n$$CH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—;
n is 1 to 5;
p is 1 to 4;
q is 1 to 4;

$R^4$ H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, or substituted $C_2$ to $C_6$ alkynyl;

$R^5$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

$R^6$ is H or $C_1$ to $C_6$ alkyl;
Q is O or S;
X is O, S, or absent;
or a pharmaceutically acceptable salt thereof.

6. The method according to claim 1, wherein said carbonyl compound is a ketone, enone, aldehyde, ester, lactone, amide, carbamate, carbonate, or enaminone.

7. The method according to claim 6, wherein said carbonyl compound is of the structure:

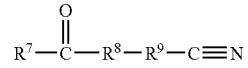

wherein:
$R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl;

$R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or $R^7$ and $R^8$ are fused to form:
(i) a saturated carbon-based 4 to 8 membered ring;
(ii) an unsaturated carbon-based 4 to 8 membered ring; or
(iii) a 4 to 8 heterocyclic ring containing 1 to 3 heteroatoms selected from the group consistinu of O, N, and S;
wherein rings (i)-(iii) are optionally substituted by 1 to 3 substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl;

$R^9$ is absent, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl;

$R^{10}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^{11}$, and $N(R^{11})_2$; and $R^{11}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

8. The method according to claim 1, wherein said carbonyl compound is of the structure:

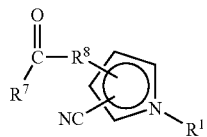

wherein:
R$^1$ is C$_1$ to C$_6$ alkyl or substituted C$_1$ to C$_6$ alkyl;
R$^7$ is H, NH$_2$, NHR$^{10}$, N(R$^{10}$)$_2$, C(O)R$^{10}$, C(S)R$^{10}$, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ thioalkyl, substituted C$_1$ to C$_6$ thioalkyl, C$_1$ to C$_6$ alkoxy, substituted C$_1$ to C$_6$ alkoxy, aryl, substituted aryl, heteroaryl, or substituted heteroaryl;
R$^8$ is C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, or substituted heteroaryl; or
R$^7$ and R$^8$ are fused to form:
(i) a saturated carbon-based 4 to 8 membered ring;
(ii) an unsaturated carbon-based 4 to 8 membered ring; or
(iii) a 4 to 8 heterocyclic ring containing 1 to 3 heteroatoms selected from the group consisting of O, N, and S;
wherein rings (i)-(iii) are optionally substituted by 1 to 3 substituents selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, substituted heteroaryl, C$_1$ to C$_6$ aminoalkyl, and substituted C$_1$ to C$_6$ aminoalkyl;
R$^{10}$ is selected from the group consisting of H, C$_1$ to C$_6$ alkyl, substituted C$_1$ to C$_6$ alkyl, aryl, substituted aryl, C$_1$ to C$_6$ alkoxy, substituted C$_1$ to C$_6$ alkoxy, C$_1$ to C$_6$ aminoalkyl, substituted C$_1$ to C$_6$ aminoalkyl, C$_1$ to C$_6$ thioalkyl, substituted C$_1$ to C$_6$ thioalkyl, NH$_2$, NHR$^{11}$, and N(R$_{11}$)$_2$; and
R$^{11}$ is selected from the group consisting of H, C$_1$ to C$_6$ alkyl, substituted C$_1$ to C$_6$ alkyl, aryl, substituted aryl, C$_1$ to C$_6$ alkoxy, substituted C$_1$ to C$_6$ alkoxy, C$_1$ to C$_6$ aminoalkyl, substituted C$_1$ to C$_6$ aminoalkyl, C$_1$ to C$_6$ thioalkyl, substituted C$_1$ to C$_6$ thioalkyl, and NH$_2$.

9. The product according to claim 1, wherein said carbonyl compound is of the structure:

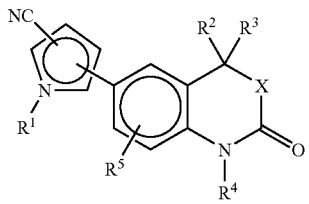

wherein:
R$^1$ is C$_1$ to C$_6$ alkyl or substituted C$_1$ to C$_6$ alkyl;
R$^2$ and R$^3$ are, independently, H, C$_1$ to C$_6$ alkyl, or substituted C$_1$ to C$_6$ alkyl;
or R$^2$ and R$^3$ are fused to form a ring comprising —CH$_2$(CH$_2$)$_n$CH$_2$—, —CH$_2$CH$_2$C(CH$_3$)$_2$CH$_2$CH$_2$—, —O(CH$_2$)$_p$CH$_2$—, —O(CH$_2$)$_q$O—, —CH$_2$CH$_2$OCH$_2$CH$_2$—, or —CH$_2$CH$_2$NR$^6$CH$_2$CH$_2$—;
n is 1 to 5;
p is 1 to 4;
q is 1 to 4;
R$^4$ is H, OH, NH$_2$, CN, halogen, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, or substituted C$_2$ to C$_6$ alkynyl;
R$^5$ is H, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, or substituted C$_1$ to C$_6$ aminoalkyl;
R$^6$ is H or C$_1$ to C$_6$ alkyl;
X is O, S, or absent;
or a pharmaceutically acceptable salt thereof.

10. The product according to claim 1, wherein said decoy agent is similar in structure to said carbonyl compound.

11. The product according to claim 1, wherein said decoy agent is acetonitrile.

12. The product according to claim 1, wherein said decoy agent comprises an electron withdrawing substituent.

13. The product according to claim 12, wherein said decoy agent is chloroacetonitrile or trichloroacetonitrile.

14. The product according to claim 1, wherein said decoy agent is an aryl nitrile selected from the group consisting of benzonitrile, p-chlorobenzonitrile, p-methoxybenzonitrile, p-ethoxybenzonitrile, o-nitrobenzonitrile, p-acetylbenzonitrile, p-methylbenzonitrile, p-fluorobenzonitrile, and 1,3-dicyanobenzene.

15. The product according to claim 1, wherein said decoy agent is a heteroaryl nitrile selected from the group consisting of N-methyl-2-pyrrolecarbonitrile, 2-thiophenecarbonitrile, 2-cyanopyridine, 3-cyanopyridine and 4-cyanopyridine.

16. The product according to claim 1, wherein said thionation is performed with a thionating agent selected from the group consisting of hydrogen sulfide, Lawesson's reagent, phosphorus pentasulfide, and diethyldithiophosphate.

17. The method according to claim 3, wherein said carbonyl compound is of the structure:

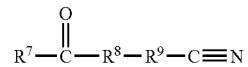

wherein:
R$^7$ is H, NH$_2$, NHR$^{10}$, N(R$^{10}$)$_2$, C(O)R$^{10}$, C(S)R$^{10}$, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ thioalkyl, substituted C$_1$ to C$_6$ thioalkyl, C$_1$ to C$_6$ alkoxy, substituted C$_1$ to C$_6$ alkoxy, aryl, substituted aryl, heteroaryl, or substituted heteroaryl;
R$^8$ is C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, C$_1$ to C$_6$ alkoxy, substituted C$_1$ to C$_6$ alkoxy, aryl, substituted aryl, heteroaryl, or substituted heteroaryl; or
R$^7$ and R$^8$ are fused to form:
(i) a saturated carbon-based 4 to 8 membered ring;
(ii) an unsaturated carbon-based 4 to 8 membered ring; or (iii) a 4 to 8 heterocyclic ring containing 1 to 3 heteroatoms selected from the group consisting of O, N, and S;
wherein rings (i)-(iii) are optionally substituted by 1 to 3 substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl;

$R^9$ is absent, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl;

$R^{10}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^{11}$, and $N(R^{11})_2$; and $R^{11}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

18. The method according to claim 3, wherein said carbonyl compound is of the structure:

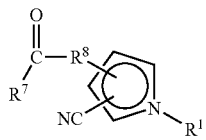

wherein:
$R^1$ is $C_1$ to $C_6$ alkyl or substituted $C_1$ to $C_6$ alkyl;
$R^7$ is H, $NH_2$, $NHR^{10}$, $N(R^{10})_2$, $C(O)R^{10}$, $C(S)R^{10}$, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ thioalkyl, substituted $C_1$ to $C_6$ thioalkyl, $C_1$ to $C_6$ alkoxy, substituted $C_1$ to $C_6$ alkoxy, aryl, substituted aryl, heteroaryl, or substituted heteroaryl;
$R^8$ is $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, or substituted heteroaryl; or
$R^7$ and $R^8$ are fused to form:
(i) a saturated carbon-based 4 to 8 membered ring;
(ii) an unsaturated carbon-based 4 to 8 membered ring; or
(iii) a 4 to 8 heterocyclic ring containing 1 to 3 heteroatoms selected from the group consisting of O, N, and S;
wherein rings (i)-(iii) are optionally substituted by 1 to 3 substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, $C_1$ to $C_6$ alkoxy, substituted $C_1$ to $C_6$ alkoxy, aryl, substituted aryl, heteroaryl, substituted heteroaryl, $C_1$ to $C_6$ aminoalkyl, and substituted $C_1$ to $C_6$ aminoalkyl;

$R^{10}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $NH_2$, $NHR^1$, and $N(R^1)_2$; and $R^{11}$ is selected from the group consisting of H, $C_1$ to $C_6$ alkyl, substituted $C_1$ to $C_6$ alkyl, aryl, substituted aryl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, and $NH_2$.

19. The method according to claim 3, wherein said carbonyl compound is of the structure:

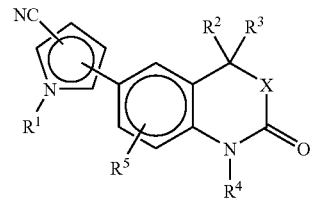

wherein:
$R^1$ is $C_1$ to $C_6$ alkyl or substituted $C_1$ to $C_6$ alkyl;
$R^2$ and $R^3$ are, independently, H, $C_1$ to $C_6$ alkyl, or substituted $C_1$ to $C_6$ alkyl;
or $R^2$ and $R^3$ are fused to form a ring comprising $—CH_2(CH_2)_nCH_2—$, $—CH_2CH_2C(CH_3)_2CH_2CH_2—$, $—O(CH_2)_pCH_2—$, $—O(CH_2)_qO—$, $—CH_2CH_2OCH_2CH_2—$, or $—CH_2CH_2NR^6CH_2CH_2—$;
n is 1 to 5;
p is 1 to 4;
q is 1 to 4;
$R^4$ is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, or substituted $C_2$ to $C_6$ alkynyl;
$R^5$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^6$ is H or $C_1$ to $C_6$ alkyl;
X is O, S, or absent;
or a pharmaceutically acceptable salt thereof.

20. The method according to claim 3, wherein said decoy agent is acetonitrile.

21. The method according to claim 3, wherein said decoy agent is chloroacetonitrile or trichloroacetonitrile.

22. The method according to claim 3, wherein said decoy agent is an aryl nitrile selected from the group consisting of benzonitrile, p-chlorobenzonitrile, p-methoxybenzonitrile, p-ethoxybenzonitrile, o-nitrobenzonitrile, p-acetylbenzonitrile, p-methylbenzonitrile, p-fluorobenzonitrile, and 1,3-dicyanobenzene.

23. The method according to claim 3, wherein said decoy agent is a heteroaryl nitrile selected from the group consisting of N-methyl-2-pyrrolecarbonitrile, 2-thiophenecarbonitrile, 2-cyanopyridine, 3-cyanopyridine and 4-cyanopyridine.

* * * * *